United States Patent [19]

Martinez

[11] Patent Number: 4,584,306
[45] Date of Patent: Apr. 22, 1986

[54] NEMATICIDAL 2-(SUBSTITUTED THIO)-4,5-DIHYDROTHIAZOLES

[75] Inventor: Anthony J. Martinez, Hamilton Square, N.J.

[73] Assignee: FMC Corporation, Philadelphia, Pa.

[21] Appl. No.: 596,759

[22] Filed: Apr. 4, 1984

[51] Int. Cl.$^4$ .................. C07D 277/10; A61K 31/425
[52] U.S. Cl. .................... 514/369; 548/182; 548/187; 71/90
[58] Field of Search ............. 424/270; 71/90; 548/182, 187

[56] References Cited

U.S. PATENT DOCUMENTS

| | | | |
|---|---|---|---|
| 2,516,313 | 7/1950 | Goddin et al. | 548/182 |
| 3,679,695 | 7/1972 | Moore et al. | 260/302 |
| 4,046,753 | 9/1977 | Fisher et al. | 260/307 |
| 4,245,033 | 1/1981 | Eida et al. | 430/353 |

FOREIGN PATENT DOCUMENTS

| | | | |
|---|---|---|---|
| 41373 | 9/1974 | Japan | 548/182 |
| 1011845 | 12/1965 | United Kingdom | 548/182 |

OTHER PUBLICATIONS

J. L. Garraway, "Growth-Regulating Activity of some Thiazole- and Thiazoline-Acetic Acids", Pestic. Sci. 1, pp. 240–243, 1970.
Chem. Abstracts 88:61941w, Hirai, K. et al.
Chem. Abstracts 81:91510c, Yamaguchi, K. et al.
Chem. Abstracts 77:114293t, Hirai, K. et al.
Chem. Abstracts 90:137721p, Vernin, G. et al.
Chem. Abstracts 94:84105q, Maeda, Ryozo et al.
Chem. Abstracts 92:128904q, Maeda, K. et al.
Hirai, K. et al., Tetrahedron Letters, (21), pp. 2117–2120 (1972).
J. R. Geigy, Chemical Abstracts, 65:1791, (1965).

*Primary Examiner*—George F. Lesmes
*Assistant Examiner*—S. A. Gibson
*Attorney, Agent, or Firm*—William Schmonsees; H. Robinson Ertelt; Robert L. Andersen

[57] ABSTRACT

Compounds of the formula

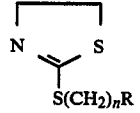

their preparation, and use for the control of nematodes are disclosed and exemplified.

3 Claims, No Drawings

NEMATICIDAL 2-(SUBSTITUTED THIO)-4,5-DIHYDROTHIAZOLES

The present invention relates to a method and composition for control of nematodes in agricultural crops and to novel nematicidal compounds. More particularly the invention relates to control of nematodes with 2-(substituted thio)-4,5-dihydrothiazole compounds and compositions.

In accordance with the method and composition aspects of the present invention, the nematicidal compounds employed are 2-(substituted thio)-4,5-dihydrothiazoles of the formula

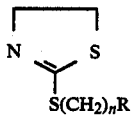

in which (A) n is zero; R is phenyl substituted with a halogen atom, with a halomethyl group, or with a nitro group; or R is a 3-($C_{1-4}$)alkylphenyl group or a 2,6-dihalophenyl group; or (B) n is 1; R is alkoxy of 1 or 2 carbon atoms, cyano, alkenyl of 2 to 4 carbon atoms, ethynyl, alkylcarbonyl or alkoxycarbonylethenyl in which the alkyl or alkoxy group has 1 or 2 carbon atoms, phenylethenyl, a tetrahydrofuranyl or thienyl group which may be substituted with a halogen atom, a furanyl group, or a 3,5-dimethylisoxazol-4-yl group.

The compounds illustrating this aspect of the invention, together with an assigned compound number and physical constants are set forth in Table I below. Certain compounds of the invention are particularly desirable for use in the method and composition aspect of this invention, notably Compound Nos. 3, 4, 5, 10, 14, 16, and 21 through 25 of Table I.

In the compound aspect of the invention most of the compounds set forth in Table I are novel compounds. However, certain of them have been disclosed in the literature for uses unrelated to nematicidal activity. In particular, Compound Nos. 3, 12, 13, 16, 18, and 20 have heretofore been reported. Of the remaining compounds, Compound Nos. 4, 10, 11, and 21 through 25 are particularly active nematicides as shown in Table II.

In accordance with the foregoing, the compound aspect of the invention comprises compounds of formula I above in which (A) n is 0 and R is selected from the group consisting of 2-chlorophenyl, 3-chlorophenyl, 2,6-dichlorophenyl, 4-bromophenyl, 4-fluorophenyl, 3-methylphenyl, 3-trifluoromethylphenyl and 4-nitrophenyl; or (B) n is 1 and R is selected from the group consisting of methoxy, cyano, —CH=CHCH₃, —CH=C(CH₃)₂, —C≡CH, —CH=CHCO₂C₂H₅, 2-tetrahydrofuranyl, 2-thienyl, 5-chloro-2-thienyl, 2-furanyl, and 3,5-dimethylisoxazol-4-yl.

The 2-(substituted thio)-4,5-dihydrothiazoles may conveniently be prepared by one of two methods. In the first method an appropriate thiol may be reacted with 2-bromoethyl isothiocyanate in the presence of a base such as triethylamine in glyme. The thiols and the 2-bromoethyl isothiocyanate are commercially available. The isothiocyanate starting material may also be prepared by the method of Garmaise, Can. J. Chem., 49, 971 (1971). Compounds Nos. 1–9, and 12 were prepared according to this method.

In the second method 2-mercaptothiazoline is reacted with the appropriate halide in the presence of a base, for example sodium hydroxide, triethylamine, or potassium carbonate and potassium iodide, in the presence of a solvent, preferably an organic solvent such as acetone, methyl ethyl ketone, tetrahydrofuran or toluene. The 2-mercaptothiazoline and most of the halides are commercially available. Those which are not com-mercially available are readily synthesized by methods well known to those skilled in the art. Compounds Nos. 10, 11, and 13-25 were prepared by this second method.

The following examples illustrate those methods of preparation.

EXAMPLE 1

Synthesis of 2-(4-chlorophenylthio)-4,5-dihydrothiazole

To a stirred solution of 2.9 grams (0.02 mole) of 4-chlorophenylthiophenol in 50 ml of glyme, under a nitrogen atmosphere, was added 2.0 grams (0.02 mole) of triethylamine. With vigorous stirring, 3.3 grams (0.02 mole) of 2-bromoethyl isothiocyanate was then added. The addition caused the reaction mixture temperature to rise to 50° C. and a solid precipitate to form. When the reaction mixture cooled to ambient temperature, it was filtered to remove the solid. The solid was washed with diethyl ether and the combined wash and filtrate were concentrated under reduced pressure to a residue. The residue was placed on a pad of silica gel and eluted with methylene chloride. The appropriate fractions were combined and concentrated under reduced pressure to give 4.0 grams of 2-(4l -chlorophenylthio)-4,5-dihydrothiazole as an oil, Compound No. 3 of Table I.

EXAMPLE 2

Synthesis of 2-(2-thienylmethylthio)-4,5-dihydrothiazole

To a stirred solution of 1.3 grams (0.011 mole) of 2-mercaptothiazoline in 20 ml of toluene was added 1.1 grams (0.011 mole) of triethylamine, followed by 1.5 grams (0.011 mole) of 2-thienylmethyl chloride. Upon completion of addition the reaction mixture was heated under reflux for five hours. The reaction mixture was cooled to ambient temperature and filtered. The filtrate was concentrated under reduced pressure to give 2.4 grams of 2-(2-thienylmethylthio)-4,5-dihydrothiazole as an oil, Compound No. 22 of Table I.

In accordance with the method and composition aspects of the invention, the compounds, like most agricultural chemicals, are generally not applied full strength, but are formulated with agriculturally acceptable carriers normally employed for facilitating the dispersion of active ingredients, various additives, and optionally with other active ingredients, recognizing that the formulation and mode of application of a toxicant may affect the activity of the material. The present compounds may be applied, for example, as powders or liquids, the choice of application varying with the nematode species and environmental factors present at the particular locus of infestation. Thus, the compounds may be formulated as granules, as dusts, as wettable powders, as emulsifiable concentrates, as solutions, as dispersions, as controlled release compositions, and the like.

A typical formulation may vary widely in concentration of the active ingredient depending on the particular agent used, the additives, carriers, or other active ingredients, used, and the desired mode of application. With due consideration to these factors, the active ingredient of a typical formulation may, for example, suitably be present at a concentration of from about 0.5% up to about 99.5% by weight to as low as about 0.5% by weight of the formulation. Surface active agents, if employed in the formulation, may be present at various concentrations, suitably in the range of 1 to 30% by weight. Provided below is a general description of exemplary types of formulations which may be employed for dispersion of the nematicides of the present invention.

Dusts are admixtures of the active ingredient with finely divided solid carriers and/or diluents such as talc, natural clays, kieselguhr, pyrophyllite, chalk, diatomaceous earths, calcium phosphates, calcium and magnesium carbonates, sulfur, lime, flours, and other organic and inorganic solid carriers. These finely divided formulations generally have an average particle size of less than about 50 microns (325 mesh, Standard U.S. Sieve Series). In most cases, the active ingredient will be present in dust formulations at a concentration in the range of 1 to 15%, and occasionally from 1% to about 30%, the balance of the composition typically comprising one or more agriculturally acceptable inerts as adjuvant, carrier, or diluent.

Wettable powders, also useful formulations for these compounds, are in the form of finely divided particles which disperse readily in water or other liquid vehicles. The wettable powder is ultimately applied as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency characteristics of the carriers. Liquids and low melting solids (mp less than 100° C.) are suitably formulated in the concentration range of 5 to 50% by weight; usually 10 to 30%; high melting solids (mp greater than 100° C.) being formulated in the range of 5 to 95% by weight, usually 50 to 85%. An agriculturally acceptable carrier or diluent, frequently including a small amount of a surfactant to facilitate wetting dispersion and suspension, accounts for the balance of the formulation.

Microencapsulated or other controlled release formulations may also be used for application of compounds in accordance with this invention.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application of the nematicide, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5% to 5% being surfactant and liquid carrier.

Flowables are similar to EC's except that the ingredient is suspended in a liquid carrier, generally water. Flowables, like EC's, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in these formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the nematicidal composition.

Other useful formulations include simple solutions of the active ingredient in a relatively non-volatile solvent such as corn oil, kerosene, propylene glycol, or other organic solvents. This type of formulation is particularly useful for ultra low volume application.

The concentration of active ingredient in use dilution is normally in the range of about 2% to about 0.1%. Many variations of spraying, dusting, and controlled or slow release compositions in the art may be used by substituting or adding a compound of this invention to compositions known or apparent to the art.

The compositions may be formulated and applied with other suitable active ingredients, including nematicides, insecticides, acaricides, fungicides, plant regulators, herbicides, fertilizers, etc.

In applying the foregoing chemicals, an effective nematode controlling amount of active ingredient must be applied, sometimes referred to herein as a nematicidal amount. While the application rate will vary widely depending on the choice of compound, the formulation and mode of application, the plant species being protected and the planting density, a suitable use rate may be in the range of 0.5 to 25 kg/hectare, preferably 1 to about 20 kg/hectare.

The compounds of this invention are usually applied by incorporating a formulation thereof into the soil in which agricultural crops are or are to be planted, i.e., the locus of infestation. This may be achieved by broadcasting the formulation over the planted area or the area to be planted or by limiting the application to a small area or band in the root zone where plants are or are to be planted. It will be readily apparent where the latter method is employed that a nematicidal amount, that is, a nematicidal concentration in the soil, must be applied to the root zone. A suitable concentration for this purpose is in the range of 0.1 to about 50 parts by weight of compound of the invention per million parts of soil.

The following are specific examples of formulations which may be utilized in accordance with the present invention:

A typical 5% dust (wt/wt) formulation is as follows:

| | |
|---|---|
| Test Compound | 5% |
| Base | 95% |
| 96% Attaclay | |
| 2% highly purified sodium lignosulfonate | (100%) |

-continued

| 2% powdered sodium alkylnapthalene sulfonate | (75%) |

A typical Attaclay granular formulation is as follows:

| Test Compound | 5% |
| Attaclay | 95% |

A typical sand core granule formulation is as follows:

| 75% base | 6.64% |
| --- | --- |
| Test Compound | 75% |
| Sodium alkylnaphthalenesulfonate | 1% |
| Sugar-free sodium based sulfonate of Kraft lignin | 4% |
| Barden clay | 20% |
| Polyvinyl acetate | 0.75% |
| Water | 1.00% |
| Silica (20/40 mesh) | 91.61% |

The Attaclay granular formulation may be prepared by dissolving the active ingredient in a volatile solvent such as methylene chloride, then coating the Attaclay with the resulting solution or by other methods well known to those skilled in the art, and allowing the solvent to evaporate. The sand core granule may be prepared by incorporating the active ingredient into a suitable base, then applying to sand to form a coated granule generally utilizing a sticker such as polyvinyl acetate.

The compounds of this invention were tested for biological activity as formulations of the active ingredient as an acetone solution, as a dust formulation, or as a granular formulation. The activity against root-knot nematode (*Meloidogyne icognita*) was determined by incorporating the compound of the invention in nematode infested soil at rates in the range of 25 ppm to 1.25 ppm. Several tomato plants were planted in the nematode infested soil. Two weeks after planting the tests were evaluated to ascertain the degree of galling on the roots of the plant, indicating the control provided by the test chemical.

The results, expressed as "knot index", are set forth in Table II. Knot index is a numerical designation assigned at evaluation, having the following meanings:

| Knot Index | Observations |
| --- | --- |
| 0 | No swellings - complete control |
| 1 | 75% less swellings than control plants |
| 2 | 50% less swellings than control plants |
| 3 | 25% less swellings than control plants |
| 4 | About same as control plants - no control. |

The results are also repeated in "percent control", a value related to knot index as follows:

| Knot Index | Percent Control |
| --- | --- |
| 0 | 100 |
| 1 | 75 |
| 2 | 50 |
| 3 | 25 |
| 4 | 0 |

When the Knot Index is between 0 and 1 it is further subdivided as follows to indicate how close the percent control is to 75% or 100%:

| Knot Index | Percent Control |
| --- | --- |
| 0.8 | 80 |
| 0.5 | 90 |
| 0.1–0.4 | 95–99 |

The results reported in Table II are the average of the knot index and percent control for each test. The compounds of this invention were highly effective against root-knot nematodes.

TABLE 1

Nematicidal 4,5-Dihydrothiazole Derivatives

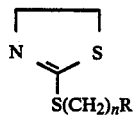

$S(CH_2)_nR$

| Cmpd No. | n | R | NMR |
| --- | --- | --- | --- |
| 1 | 0 | 2-chlorophenyl | 3.33(t,2H), 4.27(t,2H), 7.05–7.90(m,3H) |
| 2 | 0 | 3-chlorophenyl | 3.33(t,2H), 4.27(t,2H), 7.10–7.77(m,4H) |
| 3 | 0 | 4-chlorophenyl | 3.30(5,2H), 4.23(t,2H), 7.10–7.67(m,4H) |
| 4 | 0 | 2,6-dichlorophenyl | 3.37(t,2H), 4.25(t,2H), 7.10–7.67(m,3H) |
| 5 | 0 | 4-bromophenyl | 3.30(t,2H), 4.25(t,2H), 7.50(s,4H) |
| 6 | 0 | 4-fluorophenyl | 3.30(t,2H), 4.25(t,2H), 6.83–7.67(m,4H) |
| 7 | 0 | 3-methylphenyl | 2.37(s,3H), 3.27(t,2H), 4.27(t,2H), 7.17–7.57 (m,4H) |
| 8 | 0 | 3-trifluoromethylphenyl | 3.37(t,2H), 4.27(t,2H), 7.23–8.03(m,4H) |
| 9 | 0 | 4-nitrophenyl | 3.42(t,2H), 4.30(t,2H), 7.80(d,2H), 8.27(d,2H) |
| 10 | 1 | $OCH_3$ | 3.13–3.50(m,5H), 4.15 (t,2H), 5.13(s,2H) |
| 11 | 1 | CN | 3.53(t,2H), 3.93(s,2H), 4.27(t,2H) |
| 12 | 1 | $CH=CH_2$ | 3.38(t,2H), 3.78(d,2H), 4.22(t,2H), 5.00–6.32 (m,3H) |
| 13 | 1 | $C(CH_3)=CH_2$ | 1.83(d,3H), 3.40(t,2H), 3.82(s,2H), 4.28(t,2H), 4.97(d,2H) |
| 14 | 1 | $CH=CHCH_3$ | 1.70(d,3H), 3.22–4.43 (m,7H), 5.50–5.83(m,2H) |
| 15 | 1 | $CH=C(CH_3)_2$ | 1.72(bs,6H), 3.38(t,2H), 3.55–4.63(m,3H), 5.53–6.10(m,2H) |
| 16 | 1 | $CH_2CH=CH_2$ | 2.23–2.67(m,2H), 3.03–3.77(m,4H), 4.23(t,2H), 4.90–6.23(m,3H) |
| 17 | 1 | $C\equiv CH$ | 2.27(t,1H), 3.43(t,2H), 3.90(3,2H), 4.23(t,2H) |
| 18 | 1 | $CCH_3$ $\parallel$ O | 2.30(s,3H), 3.45(t,2H), 3.97(s,2H), 4.18(t,2H) |
| 19 | 1 | $CH=CHCOC_2H_5$ $\parallel$ O | 1.28(t,3H), 3.42(t,2H), 3.77–4.47(m,6H), 5.97 (d,1H), 6.73–7.32(m,1H) |
| 20 | 1 | phenylethenyl | 3.33(t,2H), 3.96(t,2H), 4.08–4.62(m, 2H), 5.97–6.80(m,2H), 7.30(bs,5H) |
| 21 | 1 | 2-tetrahydro- | 1.58–2.27(bm,4H), 3.20– |

TABLE 1-continued
Nematicidal 4,5-Dihydrothiazole Derivatives

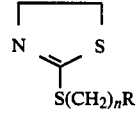

| Cmpd No. | n | R | NMR |
|---|---|---|---|
| | | furanyl | 4.40(bm,9H) |
| 22 | 1 | 2-thienyl | 3.37(t,2H), 4.23(t,2H), 4.58(2,2H), 6.77–7.33 (m,3H) |
| 23 | 1 | 5-chloro-2-thienyl | 3.47(t,2H), 4.28(t,2H), 4.50(s,2H), 6.67–6.90 (m,2H) |
| 24 | 1 | 2-furanyl | 3.37(t,2H), 4.22(t,2H), 4.38(s,2H), 6.22–6.35 (m,2H), 7.27–7.38(m,1H) |
| 25 | 1 | 3,5-dimethyl-isoxazol-4-yl | 2.28(s,3H), 2.42(s,3H), 3.42 (t,2H), 4.12(s,2H), 4.23 (t,2H) |

TABLE II
Initial Nematicidal Activity Against the Root-knot Nematode

| Cmpd No. | Application Rate (ppm) | Knot Index | Percent Control |
|---|---|---|---|
| 1 | 10 | 3.0 | 25 |
| | 2.5 | 4.0 | 0 |
| 2 | 25 | 0 | 100 |
| | 10 | 2.3 | 42 |
| | 2.5 | 3.7 | 8 |
| 3 | 25 | 0 | 100 |
| | 10 | 1.0 | 75 |
| | 10 | 0.8 | 81 |
| | 5 | 0.9 | 78 |
| | 2.5 | 1.0 | 75 |
| 4 | 25 | 0 | 100 |
| | 10 | 0 | 100 |
| | 2.5 | 1.0 | 75 |
| 5 | 25 | 0 | 100 |
| | 20 | 1.4 | 65 |
| | 2.5 | 3.7 | 8 |
| 6 | 25 | 0.8 | 80 |
| | 10 | 3.5 | 13 |
| | 2.5 | 4.0 | 0 |
| 7 | 50 | 2.5 | 38 |
| | 25 | 3.3 | 17 |
| | 5 | 3.5 | 13 |
| 8 | 25 | 1.3 | 69 |
| | 20 | 4.0 | 0 |
| 9 | 25 | 3.0 | 25 |
| | 10 | 4.0 | 0 |
| | 2.5 | 4.0 | 0 |
| 10 | 25 | 1.3 | 67 |
| | 10 | 1.7 | 58 |
| | 2.5 | 3.7 | 8 |
| 11 | 50 | 0 | 100 |
| | 25 | 0.3 | 96 |
| | 5 | 0.8 | 81 |
| 12 | 25 | 0 | 100 |
| | 10 | 0 | 100 |
| | 10 | 0 | 100 |
| | 5 | 0.3 | 97 |
| | 2.5 | 0.8 | 81 |
| 13 | 25 | 0.3 | 96 |
| | 10 | 0.9 | 78 |
| | 2.5 | 2.0 | 50 |
| 14 | 25 | 0.1 | 99 |
| | 10 | 0.9 | 77 |
| | 2.5 | 2.0 | 50 |
| 15 | 10 | 0.4 | 95 |
| | 5 | 0.8 | 81 |
| | 2.5 | 2.0 | 50 |
| 16 | 25 | 0 | 100 |
| | 10 | 0.8 | 80 |
| | 2.5 | 1.5 | 63 |
| 17 | 25 | 1.2 | 71 |
| | 10 | 3.7 | 8 |

TABLE II-continued
Initial Nematicidal Activity Against the Root-knot Nematode

| Cmpd No. | Application Rate (ppm) | Knot Index | Percent Control |
|---|---|---|---|
| | 2.5 | 4.0 | 0 |
| 18 | 25 | 1.3 | 67 |
| | 10 | 3.3 | 17 |
| | 2.5 | 4.0 | 0 |
| 19 | 25 | 2.0 | 50 |
| | 10 | 2.7 | 33 |
| | 2.5 | 3.3 | 17 |
| 20 | 10 | 1.0 | 75 |
| | 5 | — | — |
| | 2.5 | 3.7 | 8 |
| 21 | 10 | 0 | 100 |
| | 5 | 0.1 | 99 |
| | 2.5 | 0.9 | 78 |
| 22 | 25 | 0 | 100 |
| | 10 | 0.3 | 97 |
| | 2.5 | 0.3 | 96 |
| | 10 | 0.1 | 98 |
| | 5 | 0.2 | 98 |
| | 2.5 | 1.3 | 69 |
| | 1.25 | 2.0 | 50 |
| 23 | 25 | 0 | 100 |
| | 10 | 0.2 | 97 |
| | 2.5 | 3.5 | 13 |
| 24 | 25 | 0.1 | 99 |
| | 10 | 0.1 | 99 |
| | 10 | 0 | 100 |
| | 5 | 0 | 100 |
| | 2.5 | 0.17 | 98 |
| | 10 | 0.1 | 98 |
| | 5 | 0.2 | 98 |
| | 2.5 | 1.3 | 69 |
| | 1.25 | 2.0 | 50 |
| 25 | 10 | 0.5 | 95 |
| | 5 | 2.3 | 42 |
| | 2.5 | 3.5 | 13 |

I claim:

1. A method for control of nematodes in agricultural crops which comprises applying to the soil in which such crops are or are to be planted a nematicidal amount of a compound of the formula

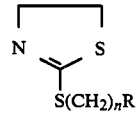

in which
  n is 1; R is a tetrahydrofuranyl or thienyl group which may be substituted with a halogen atom, or a furanyl group.

2. A nematicidal composition comprising a nematicidal amount of a compound of the formula

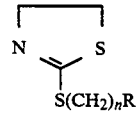

in which
  n is 1; R is a tetrahydrofuranyl or thienyl group which may be substituted with a halogen atom, or a furanyl group.

3. A nematicidal compound of the formula

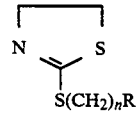

in which
  n is 1 and R is selected from the group consisting of 2-tetrahydrofuranyl, 2-thienyl, 5-chloro-2-thienyl, and 2-furanyl.

* * * * *